United States Patent [19]

Dorsey, III

[11] Patent Number: 5,281,201
[45] Date of Patent: Jan. 25, 1994

[54] HYDRODISSECTION SYSTEM

[76] Inventor: James H. Dorsey, III, 430 Commerce Dr., Ste. 50-E, Delray Beach, Fla. 33445

[21] Appl. No.: 729,987

[22] Filed: Jul. 15, 1991

[51] Int. Cl.$^5$ ............................................. A61M 1/00
[52] U.S. Cl. .................................................. 604/127
[58] Field of Search ............... 604/122, 127, 140, 254; 137/192, 399

[56] References Cited

U.S. PATENT DOCUMENTS

| | | | |
|---|---|---|---|
| 763,115 | 6/1904 | Robinson | 137/399 |
| 2,906,285 | 9/1959 | Rosten et al. | 137/399 X |
| 2,972,412 | 2/1991 | Lundeen | 137/192 X |
| 4,301,827 | 11/1981 | Murthy et al. | 137/192 X |
| 4,423,727 | 1/1984 | Widran et al. | 606/46 |
| 4,795,424 | 1/1989 | Burner | 604/30 |

Primary Examiner—Gene Mancene
Assistant Examiner—Jeffrey A. Smith
Attorney, Agent, or Firm—Malin, Haley, DiMaggio & Crosby

[57] ABSTRACT

An improved float safety mechanism (also herein "float control valve") for a gas pressurized bottle irrigation system is disclosed herein and a procedure involving the use and application thereof is also herein disclosed. In the improved safety float system of this invention, a pressurizable reservoir containing a laproscopic irrigation fluid is provided with a unique and highly reliable float or anti-siphon valve for real-time sensing of the fluid level within the reservoir and automatically terminating the withdrawal of the fluid therefrom when the level of fluid drops below a prescribed limit. The design of the anti-siphon valve used in this system is unique to the demanding pressurized environment within which the valve must function. The float safety mechanism of this invention prevents the high pressure $CO_2$ gas contained with the pressurizable reservoir from escaping (after depletion of the fluid) and entering the abdominal cavity during laparoscopy, causing possible serious or fatal injury.

9 Claims, 4 Drawing Sheets

HYDRODISSECTION SYSTEM

BACKGROUND OF THE INVENTION

1. Field of the Invention

This invention is directed to a system and to a method. More specifically, this invention relates to an improved system for use in conjunction with endoscopic instrumentation in laparoscopic surgery. This unique system incorporates a pressurizable reservoir containing the irrigation fluid, an elongated conduit, connected at the proximal end to an instrument and at its distal end to a float valve of unique design and construction wherein a sensing means in such valve can detect the level of pressurized fluid remaining in the reservoir and close the valve in response to depressed fluid level. The automatic activation of this valve in response to depression of the fluid level within the reservoir, prevents the pressurizing gas from inadvertent introduction into the operative field.

2. Description of the Prior Art

The art of endoscopy and laparoscopic surgery (and the drawbacks associated therewith) are wellknown to those skilled in the art and need not be repeated herein. Whether the endoscope is rigid or flexible, equipped with a telescope and light source or fluoroscopic means required for guidance and manipulation thereof within the operative field, one problem is generally common to both types of systems; that is, the difficulties encountered in respect to the infusion and suction of fluid into the operative field to allow for clearance, identification and targeting of the appropriate target tissue within the operative field.

The applicant has filed for patent protection on a unique "trumpet valve" for use in endoscopic surgery, application Ser. No. 07/470,771 (filed Jan. 21, 1990), now U.S. Pat. No. 5,188,591. Applicant herein incorporates by reference the discussion of the relevant art endoscopic instruments contained in such application, including the discussion of U.S. Pat. Nos. 4,191,191; 3,967,625; 4,824,434; 4,735,194; 4,795,424; 4,504,493; 4,493,320; 4,423,727; 4,217,819; and 4,795,424. The foregoing patents generally describe different endoscopic instruments and systems, and are useful as background, in appreciation of the historical development of the art endoscopy, and some of the problems associated with the art. To the extent they are relevant, reference thereto is made and is helpful as providing general background information and an aid of understanding of the instant invention.

In the operation of endoscopic instrumentation, more specifically, hydrodissection apparatus, a fluid reservoir (which reservoir is maintained under pressure) is connected through appropriate fluid channeling means to a probe tip. Typically the fluid level in the pressurized reservoir was monitored visually or was allowed to run out, such prior art systems being unreliable and often dangerous by exposure of the patient to inadvertent injection with a gas ($CO_2$).

The use of float valves in a non-pressurized and pressurized environment to control the flow of fluid from a reservoir and seal off the channel from the reservoir when the fluid drops, is well known in the prior art. The following patents are representative of different flow valve designs, and the respective operation both in ambience pressures and in a pressurized environment.

U.S. Pat. No. 3,490,482; (to Sachs, et al) describes a liquid transfer system for circulation of photographic developer, and related chemicals, within a closed loop to effect multiple batch processing of photographic film and papers.

In the context of the Sachs invention, film developer chemicals, in liquid form, are forced under pressure from a reservoir (#14) in the film developer processing loop to a developer tank (#12). Upon completion of a development process, these same fluids are recycled back to the reservoir (#14) from the developer tank (#12). This process is repeated with fixer (hypo) from reservoir (#16). In operation of the fluid transfer from the respective reservoirs, a "ball valve" (#62) partially closes the orifice leading from these respective reservoirs, allowing for compressed air to also flow from the reservoir (#16) to the developer tank (#12). The reasons for such air flow is apparently to provide a degree of agitation to the developer chemicals.

U.S. Pat. No. 2,972,412 (to Lundeen) describes a float value assembly adapted for use in a water softener system; specifically in the fluid communication of brine, from the brine storage tank, to the water softener tank. The float valve is connected to the end of a section of tubing which is positioned within the brine tank and thereby allows for the program withdrawl of brine therefrom upon cycling of the water softener tank. Fluid transfer from one tank to the other can be effected by a simple pump located in the softener tank, or by passive siphon action. When the level of brine in the brine tank drops to an unacceptable level, the float valve responds by sealing the orifice in the base of the valve, thereby preventing air from being drawn from the brine tank into the softener tank. Where the fluids transfer from one tank to the other is based upon a passive siphon system, the sealing of a valve maintains the fluid within the conduit connecting one tank to the other, thus, preserving the siphon upon the restoration of the proper fluid level in the brine tank.

U.S. Pat. No. 4,132,238 (to Clark) describes a separator valve for use in waste stream discharge systems. The valve includes a cage and a float. The materials from which the float is constructed allow for movement thereof within the cage in response to changes in the specific gravity of the waste water discharge. Where the discharge is essentially oil free, that is, has a specific gravity approximating the specific gravity of the water, the float will remain buoyant. Where the specific gravity of the discharge drops below the specific gravity of the water, the float will respond by losing its buoyancy and moving to the floor of the cage, thereby sealing a orifice in the base of the cage, and preventing further discharge of the waste stream through the valve.

U.S. Pat. No. 3,227,173 (to Bernstein) describes a series of flotation type valves adapted for use in the clinical environment. All of the embodiments of the Bernstein concept involve the placement of a float within a container at least partially filled with a parenternal fluid. As parenternal fluid is passively (IV) or actively (syringe) withdrawn from the fluid container, these valves respond to the depressed fluid level within the container by sealing an orifice through which such fluid must pass.

U.S. Pat. No. 4,078,563 (to Tuseth) describes a disk valve for control of withdrawal of parenternal fluid from an inverted container. The valve is positioned within the neck of the container, and responds to withdrawal of fluid therefrom in much the same way as the more traditional design illustrated in the Bernstein patent discussed above.

As is evident from the foregoing, the use and adaptation of float valves to control, meter and arrest the flow of fluid from a container to a variety of environments and fluid containment vessels. The design of each float valve will of course vary with the specific vessel design, the fluid composition and the means used to effect transfer of fluid from its container through its valve to the discharge/withdrawal site.

As is further evident from the foregoing, valves are typically used in systems involving a passive transfer mechanism, that is fluid flow from the container through the float valve is generally accomplished by a combination gravity and siphon action. Where, however, fluid transfer is effected by means of an active transport mechanism, such as by pressurization of the fluid container, both the rate of fluid transfer and depression in the fluid level in the fluid reservoir will be greatly accelerated. In such an active fluid transport system, valve response must be more rapid and precise in order to avoid withdrawal of fluid below the level that is prescribed for such a system. This is particularly critical in dispensing of chemical fluids and in their use in endoscopic systems. Traditionally, the transfer of fluid in such active transport (endoscopic) systems has been monitored electronically. The valving in such system is typically effected through solenoid activation upon optical and/or electronic pressure sensing of fluid level. Notwithstanding the availability of such electronically activated systems, the float valve has been and remains the mechanism of choice. Unfortunately, such valves have typically lacked the response time and the precision necessary to effectively seal off fluid flow from a pressurized container and/or reservoir.

OBJECT OF THE INVENTION

It is the object of this invention to remedy the above as well as related deficiencies in the prior art.

More specifically, it is the primary object of the invention to provide a system adapted for the performance of laparoscopic irrigation and hydrodissection procedures having a pressurized fluid reservoir wherein the fluid level in the reservoir is mechanically monitored by a float valve of unique design and construction.

It is another object of this invention to provide a hydrodissection system wherein the float valve, within the pressurized vessel containing the hydrodissection fluid, senses the fluid level and automatically closes and/or seals an orifice leading from the reservoir to a fluid withdrawing conduit, thus, preventing escape of pressurizing gas from the reservoir through the valve.

It is yet another object of this invention to provide a fail safe method for preventing the escape of gas from a pressurized reservoir utilized in hydrodissection and other related environments.

It is yet another object of this invention to provide an endoscopic instrument system incorporating the unique features and operational advantages of the improvements described hereinafter in detail.

SUMMARY OF THE INVENTION

The above and related objects of this invention are achieved by providing a float valve of unique design and construction to effect-real time monitoring and control of the level of fluid as it is withdrawn from a pressurized reservoir, and sealing off of the fluid channel leading from the reservoir to a laproscopic instrument, so as to prevent escape of pressuring gas from the reservoir through the fluid channel. The design of the float valve includes a valve housing having a trace within said housing for containment and guidance of a buoyant body; and, a fluid channel within said housing, said channel being provided at one end with a valve seat adapted for sealing engagement with the buoyant body and, at the opposite end, with means for attachment to a fluid withdrawing conduit, external to the valve body. The configuration of the trace within the housing is designed for effective guidance and rapid movement of the buoyant body relative to the valve seat to achieve essentially real-time response to depression in the fluid level, and complete sealing of the fluid channel leading from the pressurized reservoir to a laproscopic instrument.

In the preferred embodiments of this invention, the trace conforms, in general and overall configuration, to an inverted "T"; that is having an essentially vertical component connected to a horizontal component; the point of connection of the vertical component to the horizontal component being approximately equidistant from each end of the horizontal component.

In the preferred embodiments of this invention, the component of the fluid channel, defined by and internal to, the valve housing, is in fluid communication with the valve seat at the base of the float valve, and generally parallels the trace as it leads from the valve seat to the conduit external to the valve housing. The diameter of the opening leading from the valve seat to the fluid channel is approximately the same as that of the fluid channel, or less than the diameter of the fluid channel.

In operation of the hydrosection system of this invention, the reservoir contains a hydrodissection fluid, under pressure, and a valve connected to channelling means, which provides for communication of the fluid contents of the vessel with the laproscopic instrument. The laproscopic instrument is provided with controls to effect withdrawal of fluid from the reservoir. As fluid is withdrawn from the reservoir, the fluid level within the reservoir will be depressed, and, depending upon the length of the operative procedure may be reduced to a point where pressurizing gas in the reservoir, can also be inadvertently withdrawn through the fluid channel. In order to prevent the withdrawal of pressurizing gas from the reservoir into the fluid communicating channel and then into the patient, the buoyant body within the trace of the valve will respond to depression in the fluid level by moving within the trace, from the top of the trace toward to valve seat as fluid level is reduced. In the preferred embodiment of this invention, the valve trace, as heretofore described, comprises an inverted "T" in overall design and construction, thus, allowing for rapid and real-time response of the buoyant body to depression in the fluid level and essentially complete sealing of the valve seat to prevent inadvertent withdrawal of gas from the pressurized vessel and thereby prevent any potential injury to the patient undergoing the laproscopic procedure.

BRIEF DESCRIPTION OF THE DRAWINGS

The objectives and advantages described above as well as others, and the device and its method of operation will be better understood from the description below and the appended drawings in which.

DETAILED DESCRIPTION OF THE INVENTION INCLUDING PREFERRED EMBODIMENTS

Figure 1:
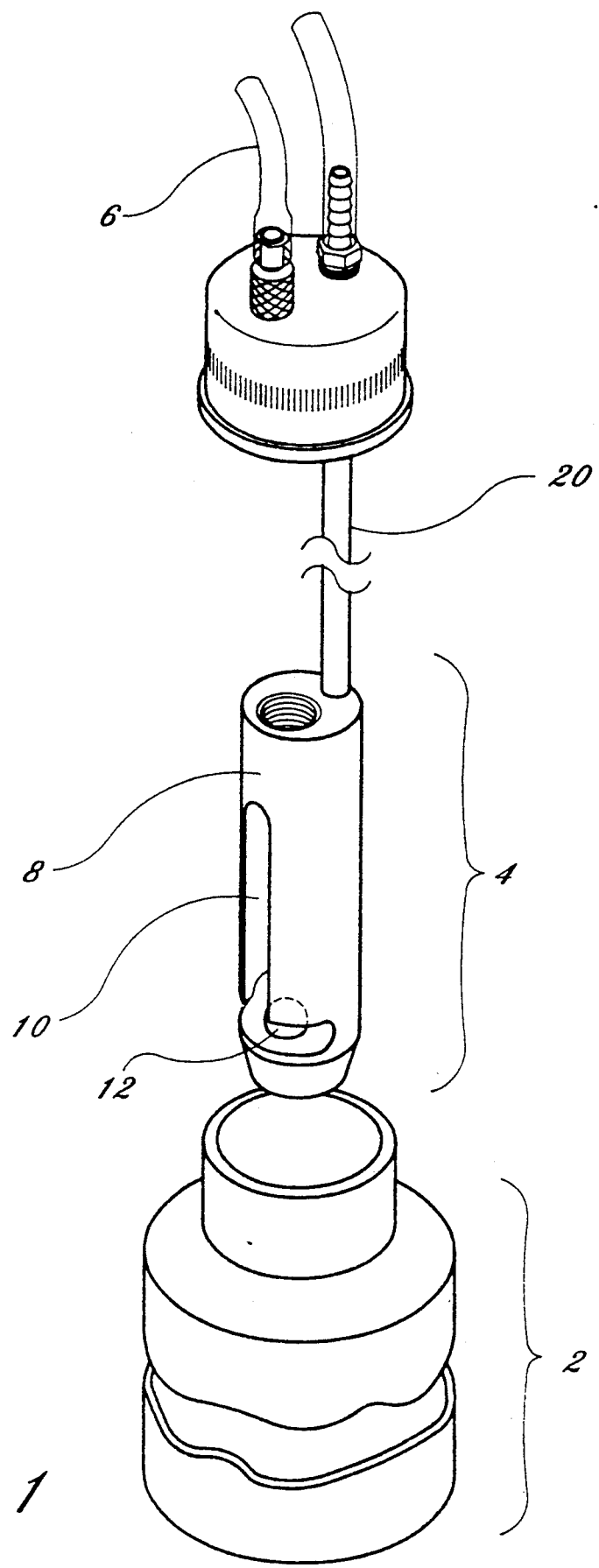
FIG. 1 is a plan view of the pressurized vessel for hydrodissection device system disclosed herein showing the float valve in accordance with the present invention.

The invention is hereinafter described in reference to FIGS. 1-4. Where a component appears in two (2) or more figures, it is assigned a common reference numeral for ease of identification and discussion.

FIG. 1 illustrates a pressurized reservoir (2) wherein a float control valve (4) is connected to a fluid conduit (6) leading from such valve to an endoscopic instrument (not shown). The components of the float valve, as illustrated in FIG. 1, includes a housing (8), a trace (10) defined within the housing (8) and a buoyant body (12) which is constrained within the confines of the trace (10). The illustration of the invention in FIG. 1 depicts the buoyant body at or near the bottom of the trace (which is defined by a valve seat).

Figure 2:
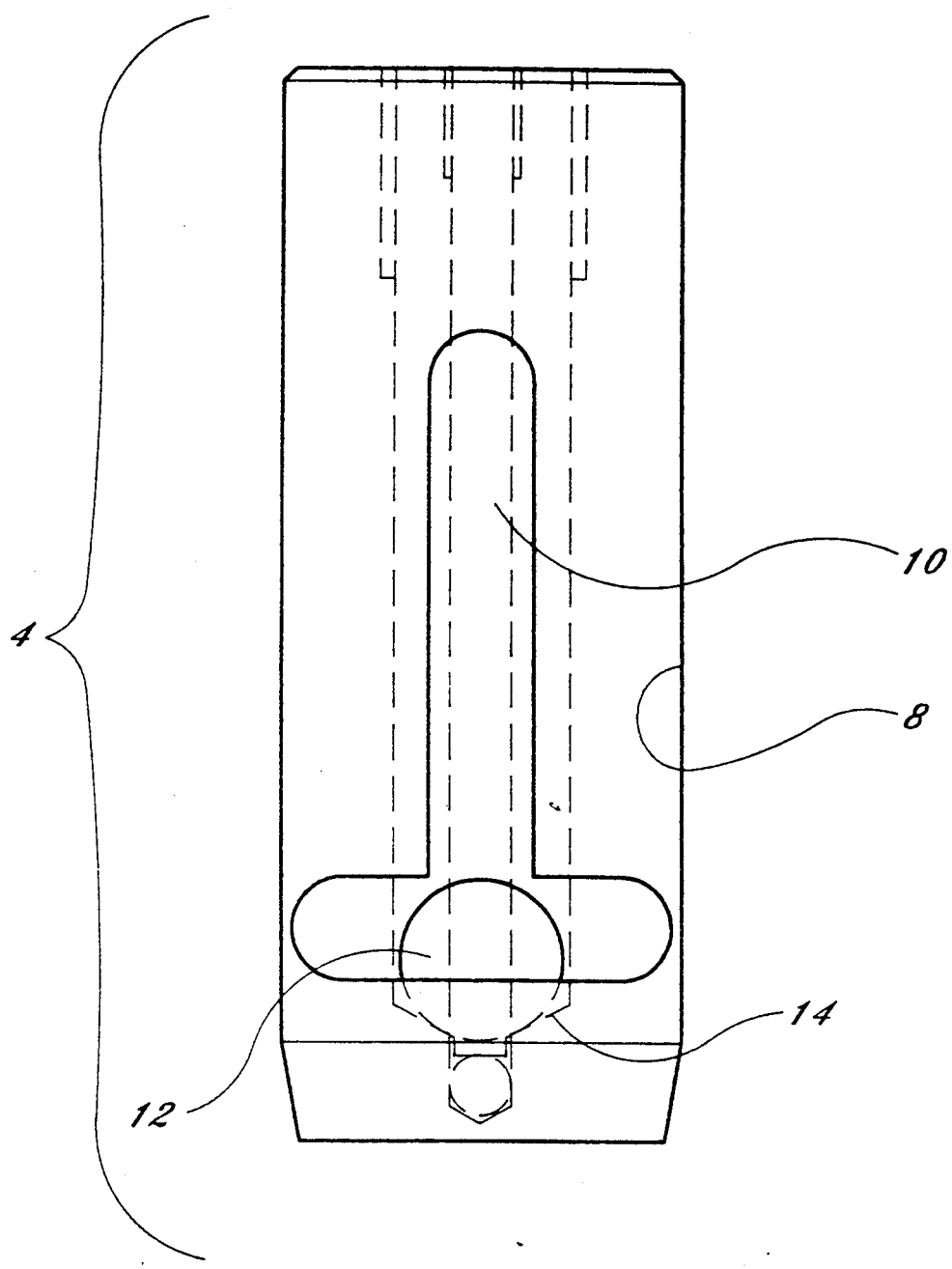
FIG. 2 is an enlarged plan view of the float valve used as part of the improved hydrodissection system disclosed herein.
Figure 3:
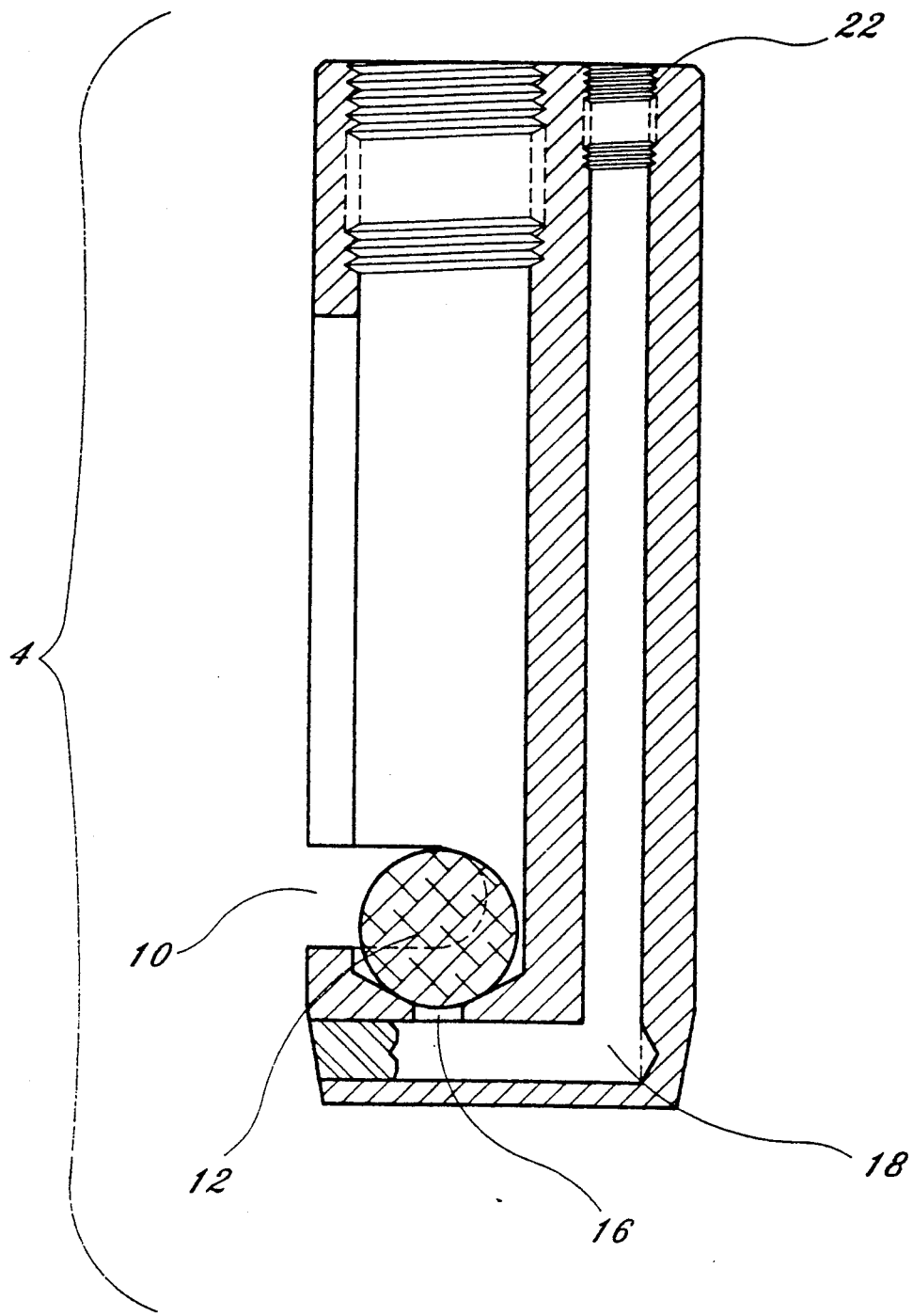
FIG. 3 is a sectional view, along Line A—A, of the float valve shown in FIG. 2.
Figure 4:
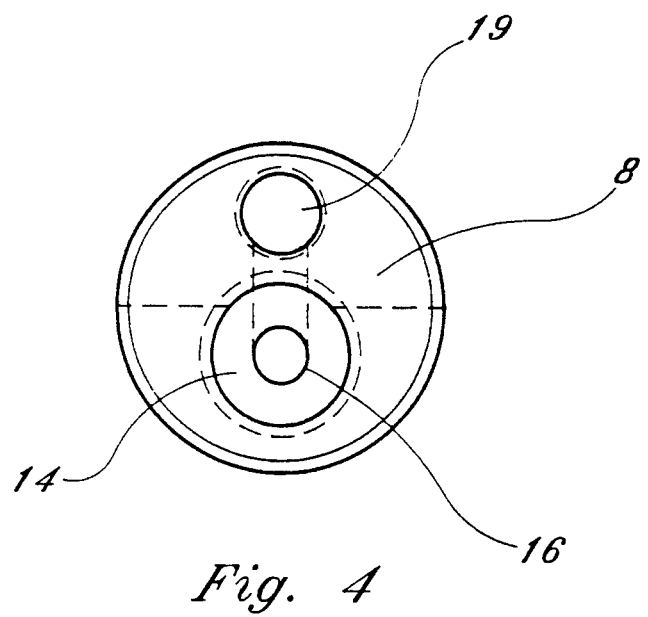
FIG. 4 is an enlarged sectional view of the float valve housing at the level of the valve seat.

As more fully illustrated in FIG. 2, the trace (10) conforms in overall configuration to an inverted "T", wherein the top of the "T" defines the upper limits of travel of the buoyant body within the housing; and, the bottom of the trace, the lower limits of travel of the buoyant body, or the valve seat (14). As more fully illustrated in FIG. 3, the trace exposes the buoyant body to fluid within the pressurized vessel from at least three (3) sides, thus, allowing for rapid response time of the buoyant body to depression in the fluid level within the pressurized vessel. As also illustrated in FIG. 3, the relative proportions of the opening (16) (diameter) in the valve seat (14) and the fluid communication channel (18) directly affect response time of the valve. More specifically, by matching the buoyancy of the buoyant body, the rate of fluid withdrawal, the opening of the valve seat and the contemplated pressure within the pressurized vessel the improved float valve of this invention achieves real-time sensing of depressed fluid levels in the pressurized reservoir and effective and essentially complete sealing of the valve seat with the buoyant body upon depression of the fluid level to a point where further removal would potentially cause escape of pressuring gas into the fluid communication channel. FIG. 4 further illustrates the relationships as heretofore described in reference to FIG. 3. More specifically, the relative diameter of the opening in the valve seat (16) to the fluid communication channel (18) is pre-determined so as to accomplish the aforestated objectives of this invention, namely the real-time sensing of the fluid level within the pressurized vessel and essentially complete sealing of the opening in the valve seat upon depression of that fluid level to a point where escape of pressurizing gas into the fluid communication channel is possibility.

In operation of the safety float system of this invention, a conduit (20) is connected to the fluid communication channel (18) within the valve housing at the top (22) of the float valve. Upon withdrawal of fluid from the pressurized vessel, the fluid is conducted to a laproscopic instrument, such as a trumpet valve device. The fluid withdrawal is controlled through means (i.e.) trumpet valve as per copending U.S. application Ser. No. 07/470,771, filed Jan. 26, 1990, now U.S. Pat. No. 5,188,591, associated with the laparoscoping instrument and in order to effect delivery to the target tissue within an operative field.

In one of the alternative embodiments of this invention, a plurality of pressurized reservoirs can be connected to a common conduit supplying fluid to the laproscopic instrument and automatically activated upon sensing of resistance to withdrawal of fluid from the first pressurized vessel, thus, providing for an essentially continuous flow of fluid to the laproscopic instrument.

The foregoing invention has been described in reference to certain preferred embodiments thereof as depicted in FIGS. 1-4. It is appreciated that such description has been provided as simply illustrative of the invention and not intended to define its scope which is set forth in the following Claims.

What is claimed is:

1. A device, operatively associated with a fluid withdrawing conduit disposed within a reservoir containing a fluid or other contents, for preventing pressurized gas from entering the fluid withdrawing conduit when the fluid reaches a certain level within the reservoir, comprising:

a housing having a first end, a second end and a side wall and defining a trace chamber disposed within, said trace chamber having an inverted "T" shape configuration, said trace chamber extending through the side wall of said housing for direct exposure to the contents of the reservoir, said housing having a first substantially vertically oriented fluid communication channel disposed within and extending from the first end of said housing to a first substantially horizontal fluid communication channel, the first vertically oriented fluid communication channel and said trace chamber being fluidly communicated by the horizontal fluid communication channel;

a buoyant body member contained within and guided by said trace chamber, said buoyant body member providing a quick and complete seal of communication between the trace member and the first horizontally oriented fluid communication channel to prevent the pressurized gas disposed within the reservoir from entering the first vertically oriented fluid communication channel, and thus the fluid withdrawing conduit, when the fluid disposed within the reservoir drops to a certain level.

2. The device of claim 1 further including a valve seat member having a opening and disposed within said housing between the horizontally oriented fluid communication channel and the trace chamber, said valve seat member providing fluid communication between said trace chamber and said horizontally oriented fluid communication channel, said valve seat member receiving said buoyant body member when the fluid disposed within the reservoir drops to a certain level.

3. The device of claim 2 wherein the opening of said valve seat member and the horizontally oriented fluid communication channel are sized in diameter to provide essentially real-time sensing of the level of fluid disposed within the reservoir to allow complete sealing of the opening of said valve seat member by said buoyant body member upon the depression of the fluid level to a point where escape of the pressurized gas disposed within the reservoir into the horizontally oriented fluid communication channel would be possible.

4. The device of claim 1 wherein the first vertically oriented fluid communication channel is operatively associated with the fluid withdrawing conduit at the first end of said housing.

5. The device of claim 1 wherein said housing further includes a second substantially vertically oriented fluid communication channel disposed within and extending from and through the first end of said housing to said trace chamber, the second vertically oriented fluid communication channel providing fluid communication between the reservoir and said trace chamber.

6. A float valve device, operatively associated with a fluid withdrawing conduit disposed within a reservoir containing a fluid, for preventing pressurized gas from entering the fluid withdrawing conduit when the fluid reaches a certain level within the reservoir, comprising:

a housing having a first end, a second end and a side wall and defining an inverted "T"-shaped trace chamber disposed within, said trace chamber extending through the side wall of said housing for direct exposure to the fluid and pressurized gas disposed within the reservoir, said housing having a first substantially vertically oriented fluid communication channel disposed within and extending from the first end of said housing to a first substantially horizontal fluid communication channel, said housing having a valve seat member disposed within between the horizontally oriented fluid communication channel and the trace chamber, said valve seat member having an opening, the first vertically oriented fluid communication channel and trace chamber being fluidly communicated through the horizontal fluid communication channel and valve seat member;

a buoyant body member contained within and guided by said trace chamber, said buoyant member received by said valve seat member to provide a quick and complete seal of communication between the trace chamber and the first vertically oriented fluid communication channel to prevent the pressurized gas disposed within the reservoir from entering the first vertically oriented fluid communication channel, and thus the fluid withdrawing conduit, when the fluid disposed within the reservoir drops to a certain level.

7. The device of claim 6 wherein the first vertically oriented fluid communication channel is operatively associated with the fluid withdrawing conduit at the first end of said housing.

8. The device of claim 6 wherein the opening of said valve seat member and the horizontally oriented fluid communication channel are sized in diameter to provide essentially real-time sensing of the level of fluid disposed within the reservoir to allow complete sealing of the opening of said valve seat member by said buoyant body member upon the depression of the fluid level to a point where escape of the pressurized gas disposed within the reservoir into the horizontally oriented fluid communication channel would be possible.

9. The device of claim 6 wherein said housing further includes a second substantially vertically oriented fluid communication channel disposed within and extending from the first end of said housing to said trace chamber, the second vertically oriented fluid communication channel providing fluid communication between the reservoir and said trace chamber.

* * * * *